United States Patent [19]

Hirohashi et al.

[11] 4,001,412
[45] * Jan. 4, 1977

[54] 1-SUBSTITUTED-1,2-DIHYDROTHIENO[2,3-d]-PYRIMIDIN-2-ONE DERIVATIVES

[75] Inventors: Toshiyuki Hirohashi, Ashiya; Hiromi Sato; Shigeho Inaba, both of Takarazuka; Hisao Yamamoto, Nishinomiya, all of Japan

[73] Assignee: Sumitomo Chemical Company, Limited, Osaka, Japan

[ * ] Notice: The portion of the term of this patent subsequent to May 18, 1993, has been disclaimed.

[22] Filed: May 6, 1975

[21] Appl. No.: 575,042

Related U.S. Application Data

[63] Continuation of Ser. No. 335,775, Feb. 26, 1973, abandoned.

[30] Foreign Application Priority Data

Feb. 28, 1972 Japan .............................. 47-20357

[52] U.S. Cl. .......................... 424/251; 260/251 A; 260/256.4 F; 260/256.5 R; 260/247.2 A; 260/247.7 R; 260/247.7 V; 260/247.7 Z; 260/293.57; 260/332.3 R; 260/330.5; 260/329 AM; 260/332.2 R
[51] Int. Cl.² .............. C07D 495/04; A61K 31/495
[58] Field of Search ................. 260/251 A; 424/251

[56] References Cited

UNITED STATES PATENTS 3,830,813    8/1974    Woitum et al. ............ 260/256.5 R

OTHER PUBLICATIONS

Robba et al., Chemical Abstracts v. 70, 37,767b (1969).
Robba et al., Chemical Abstracts, v. 69, 27,365j (1968).
Robba et al., Chemical Abstracts, v. 69, 96,635j (1968).
Sauter, Chemical Abstracts, v. 69, 96,647q (1968).
Gronowitz et al., Chemical Abstracts, v. 70, 87,745p (1969).
Manhas et al., Chemical Abstracts, v. 71, 101,801h (1969).
Schweizer et al., Chemical Abstracts, v. 72, 90,498g (1970).
Manhas et al., Chemical Abstracts, v. 76, 107,846b (5/8/72).

*Primary Examiner*—Donald G. Daus
*Assistant Examiner*—Diana G. Rivers
*Attorney, Agent, or Firm*—Stevens, Davis, Miller & Mosher

[57] ABSTRACT

1-Substituted-1,2-dihydrothieno[2,3-d]-pyrimidin-2-ones of the formula,

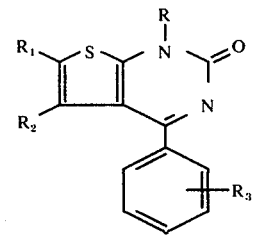

wherein R is lower alkyl or cyclopropylmethyl, $R_1$ is halogen, lower alkyl or nitro, $R_2$ is hydrogen or lower alkyl and $R_3$ is hydrogen or halogen, are obtained by treating a trihaloacetamidothiophene derivative with ammonia. These compounds have excellent pharmacological activities such as uricosuric activity.

13 Claims, No Drawings

1-SUBSTITUTED-1,2-DIHYDROTHIENO[2,3-D]-PYRIMIDIN-2-ONE DERIVATIVES

This is a continuation of application Ser. No. 335,775 filed Feb. 26, 1973, now abandoned.

DESCRIPTION OF THE INVENTION:

This invention relates to novel thienopyrimidine derivatives and a process for production thereof. More particularly, the present invention is concerned with novel thienopyrimidine derivatives represented by the formula,

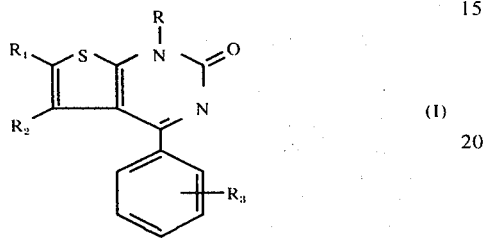

wherein $R_1$, $R_2$ and $R_3$ are independently hydrogen, a lower alkyl, lower alkoxy, nitro, trifluoromethyl group, lower alkylthio group, lower alkylsulfonyl or a halogen atom; and R is hydrogen, lower alkyl, lower alkenyl aralkyl, lower alkoxyalkyl, cycloalkylalkyl, lower haloalkyl, lower alkylthioalkyl, lower alkoxycarbonylalkyl group, lower alkanoyloxyalkyl, or a of the formula,

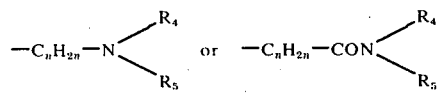

wherein $n$ is an integer of 1 to 3; and $R_4$ and $R_5$ are independently alkyl provided that $R_4$ and $R_5$ may form together with the adjacent nitrogen atom an unsubstituted or optionally substituted 5- or 6-membered heterocyclic ring, which may further contain a hetero atom.)

In the compounds represented by the general formula (I), the term "alkyl" means either straight or branched chain aliphatic hydrocarbon radical, and the lower alkyl includes, for example, methyl, ethyl, n-propyl, isopropyl, n-butyl, isobutyl and tertiarybutyl; the lower alkoxy includes, for example, methoxy, ethoxy, n-propoxy, isopropoxy, n-butoxy and tertiary-butoxy; the lower alkylthio includes, for example, methylthio, ethylthio and butylthio; the term "halogen" comprehends all halogens (e.g. fluorine, chlorine, bromine and iodine); the lower alkylsulfonyl includes, for example, methylsulfonyl and ethylsulfonyl; the lower alkoxyalkyl includes, for example, methoxymethyl, ethoxyethyl and methoxyethyl; the cycloalkylalkyl includes, for example, cyclopropylmethyl, cyclobutylmethyl and cyclohexylmethyl; the lower haloalkyl includes, for example, chloroethyl, chloropropyl and chlorobutyl; the alkylthioalkyl includes, for example, methylthioethyl, ethylthiomethyl and methylthiomethyl; the alkoxycarbonylalkyl includes, for example, methoxycarbonylmethyl and ethoxycarbonylmethyl; the alkanoyloxyalkyl includes, for example, acetoxyethyl and propionyloxyethyl; the lower alkenyl includes, for example, vinyl, allyl, methallyl, butenyl and crotyl; the aralkyl includes, for example, benzyl, phenethyl, chlorobenzyl and fluorobenzyl. The alkylene represented by $C_nH_{2n}$ is a straight chain or branched chain alkylene having 1 to 3 carbon atoms, and includes, for example, methylene, ethylene, 1-methylethylene, 2-methylethylene and trimethylene. $R_4$ and $R_5$ may form together with the adjacent nitrogen atom a heterocyclic ring, and the heterocyclic group includes, for example, pyrrolidino, piperidino and morpholino and substituted derivatives thereof.

In accordance with the present invention, thienopyrimidine compounds of the Formula (I) are produced by treating with ammonia a trihaloacetamidothiophene derivative of the formula,

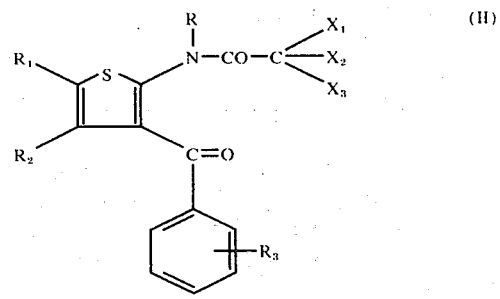

wherein $R_1$, $R_2$, $R_3$ and R are as defined above in the formula (I) and $X_1$, $X_2$ and $X_3$ are independently halogen atoms.

The trihaloacetamidothiophene derivatives of the formula (II) which are employed in the present invention can be, for example, prepared by contacting a 2-aminothiophene derivative with a trihaloacetic acid or its reactive derivative.

In preparing the thienopyrimidine derivatives, the trihaloacetamidothiophene derivative represented by the aforesaid general formula (II) is reacted with ammonia preferably in the presence of a solvent.

Examples of the solvent include methanol, ethanol, isopropanol, tertiary-butanol, Cellosolve, tetrahydrofuran, dioxane, benzene, toluene, acetone, acetonitrile, pyridine, dimethyl-sulfoxide, dimethylformamide and a mixture thereof.

Ammonia can be added to the reaction mixture as gaseous ammonia, an alcoholic ammonia (e.g. methanolic ammonia or ethanolic ammonia), liquid ammonia or an ammonium salt (e.g. ammonium acetate, ammonium formate, ammonium carbamate, ammonium phosphate or ammonium carbonate) which generates ammonia during the reaction.

Generally, the reaction proceeds at room temperature, but the temperature may be higher or lower, if necessary, to effect a desired control of the reaction.

The thienopyrimidine derivative of the formula (I), which has not been described in any literature, have excellent antiinflammatory, uricosuric and diuretic activities, with low toxicities. For example, 1-methyl-4-(o-fluorophenyl)-6-methyl-1,2-dihydrothieno-(2,3-d)-pyrimidin-2-one has remarkably potent uricosuric activity, which has never reported in any literature. Details are as shown below.

EFFECT ON URIC ACID EXCRETION IN MICE

Mice of ddN strain, weighing 18 g to 20 g, were used. After the intravenous injection of 20 mg per kilogram of the body weight of uric acid, they were given oral does of test compounds in amount of 100 mg per kilogram of the body weight. Urine of each group of mice, consisted of 4 animals each, was collected for 5 hours following the dose and the concentration of uric acid in urine was determined by Caraway's method (W. T. Caraway: American Journal of Clinical Pathology, volume 25, page 840 (1955)).

The results are shown in the Table.

Table:

| | Effect on excretion of uric acid in mice |
|---|---|
| Compounds | Uric acid excreted ($\mu$g/100 g of body weight) |
| 1-Methyl-4-(o-fluorophenyl)-6-methyl-1,2-dihydrothieno-(2,3-d)-pyrimidin-2-one | 119 |
| Probenecid | 24 |
| Non-medicated Control | 14 |

1-Methyl-(o-fluorophenyl)-6-methyl-1,2-dihydrothieno-(2,3-d)-pyrimidin-2-one showed greater excretion of uric acid than the reference compound, probenccid, which is most widely used as a uricosuric agent in the world.

Thienopyrimidines of the present invention can be administered parenterally or orally in any of the usual therapeutic dosage forms with dosage adjusted to individual needs, that is, in solid or liquid dosage forms such as tablets, dragies, capsules, suspensions, solutions, elixirs and the like. The dosage of the present therapeutic agents may vary from 0.2 to 50 mg per kg of bodyweight per day with the form of administration and the particular compound chosen.

According to the process of the present invention, there are produced, for example, the following thienopyrimidine derivatives:

1-Methyl-4-phenyl-1,2-dihydrothieno(2,3-d)-pyrimidin-2-one, m.p. 256°–257.5° C.

1-Methyl-4-phenyl-6-chloro-1,2-dihydrothieno-(2,3-d)-pyrimidin-2-one, m.p. 136°–140° C.

1-Methyl-4-phenyl-6-nitro-1,2-dihydrothieno(2,3-d)-pyrimidin-2-one, m.p. 272°–274° C.

1-Cyclopropylmethyl-4-phenyl-1,2-dihydrothieno(2,3-d)-pyrimidin-2-one, m.p. 191°–191.5° C.

1-Cyclopropylmethyl-4-phenyl-6-nitro-1,2-dihydrothieno(2,3-d)-pyrimidin-2-one, m.p. 216°–218° C.

1-Cyclopropylmethyl-4-phenyl-6-chloro-1,2-dihydrothieno(2.3-d)-pyrimidin-2-one, m.p. 149°–151° C.

1-Methyl-4-(o-fluorophenyl)-1,2-dihydrothieno-(2,3-d)-pyrimidin-2-one, m.p. 222°–223° C.

1-Methyl-4-(o-fluorophenyl)-6-chloro-1,2-dihydrothieno(2,3-d)-pyrimidin-2-one, m.p. 192.5°–194° C.

4-(o-Fluorophenyl)-6-methyl-1,2-dihydrothieno-(2,3-d)-pyrimidin-2-one, m.p. 282°–284° C.

1-Methyl-4-(o-chlorophenyl)-1,2-dihydrothieno-(2,3-d)-pyrimidin-2-one, m.p. 225°–226° C.

1-Methyl-4-phenyl-5-methyl-1,2-dihydrothieno-(2,3-d)-pyrimidin-2-one, m.p. 281°–283° C.

1-Methyl-4-(o-fluorophenyl)-5-methyl-1,2-dihydrothieno(2,3-d)-pyrimidin-2-one, m.p. 275°–277° C.

1-Methyl-4-(o-fluorophenyl)-6-methyl-1,2-dihydrothieno(2,3-d)-pyrimidin-2-one, m.p. 119°–121° C.

1-Methyl-4-(o-fluorophenyl)-5-methyl-6-chloro-1,2-dihydrothieno(2,3-d)-pyrimidin-2-one, m.p. 175°–176° C.

1-Methyl-4-(o-chlorophenyl)-6-chloro-1,2-dihydrothieno(2,3-d)-pyrimidin-2-one, m.p. 164°–166° C.

1-Methyl-4-phenyl-5-methyl-6-chloro-1,2-dihydrothieno(2,3-d)-pyrimidin-2-one, m.p. 192°–194° C.

1-Methyl-4-(o-chlorophenyl)-5-methyl-1,2-dihydrothieno(2,3-d)-pyrimidin-2-one, m.p. 267.5°–268.5° C.

1-Methyl-4-(o-chlorophenyl)-5-methyl-6-chloro-1,2-dihydrothieno(2,3-d)-pyrimidin-2-one, m.p. 199.5°–200.5° C.

1-Cyclohexylmethyl-4-phenyl-1,2-dihydrothieno(2,3-d)-pyrimidin-2-one.

1-Cyclohexylmethyl-4-phenyl-6-nitro-1,2-dihydrothieno(2,3-d)-pyrimidin-2-one.

4-Phenyl-6-trifluoromethyl-1,2-dihydrothieno-(2,3-d)-pyrimidin-2-one.

4-Phenyl-6-methylthio-1,2-dihydrothieno(2,3-d)-pyrimidin-2-one.

4-Phenyl-6-methoxy-1,2-dihydrothieno(2,3-d)-pyrimidin-2-one.

4-Phenyl-6-methylsulfonyl-1,2-dihydrothieno-(2,3-d)-pyrimidin-2-one.

1-Methyl-4-(p-chlorophenyl)-1,2-dihydrothieno-(2,3-d)-pyrimidin-2-one.

1-Benzyl-4-phenyl-1,2-dihydrothieno(2,3-d)-pyrimidin-2-one.

1-($\beta$-Ethoxyethyl)-4-phenyl-1,2-dihydrothieno-(2,3-d)-pyrimidin-2-one.

1-($\beta$-Acetoxyethyl)-4-phenyl-1,2-dihydrothieno-(2,3-d)-pyrimidin-2-one.

1-(Methoxycarbonylmethyl)-4-phenyl-1,2-dihydrothieno(2,3-d)-pyrimidin-2-one 1-(N-Methylcarbamoylmethyl)-4-phenyl-1,2-dihydrothieno(2,3-d)-pyrimidin-2-one.

1-($\beta$-Methylthioethyl)-4-phenyl-1,2-dihydrothieno-(2,3-d)-pyrimidin-2-one.

1-Allyl-4-phenyl-1,2-dihydrothieno(2,3-d)-pyrimidin-2-one.

1-($\beta$-Diethylaminoethyl)-4-phenyl-1,2-dihydrothieno(2,3-d)-pyrimidin-2-one.

1-($\beta$-Morpholinoethyl)-4-phenyl-1,2-dihydrothieno(2,3-d)-pyrimidin-2-one.

This invention is further disclosed in the following Examples of more preferred embodiments thereof, which are presented for the purpose of illustration and it is not intended to limit the scope of the invention.

EXAMPLE 1

To a solution of 2.0 g of 2-trichloroacetamido-3-benzoylthiophene in 18 ml of dimethylsulfoxide was added 0.89 g of ammonium acetate. The mixture was heated at 95° C for 2 hours, and poured into ice water, and extracted with chloroform. The chloroform layer was washed with water, dried over sodium sulfate, and the solvent was removed under reduced pressure. The residue was chromatographed on 60 g of silica gel, using methanol as an eluent to obtain 4-phenyl-1,2-dihydrothieno(2,3-d)-pyrimidin-2-one as crystals. Recrystallized from chloroform-acetone, the crystals having a melting point of 247.5°–249° C. were obtained.

EXAMPLE 2

To a solution of 2.11 g of 2-trichloroacetamido-3-(o-fluorobenzoyl)thiophene in 18 ml of dimethylsulfoxide was added 0.89 g of ammonium acetate. The mixture was heated at 95° C for 2 hours and poured into ice water, and extracted with dichloromethane. The dichloromethane layer was washed with water, dried over sodium sulfate and the solvent was removed under reduced pressure. The residue was chromatographed on 60 g of Silica gel, using ethyl acetate as an eluent to obtain 4-(o-fluorophenyl)-1,2-dihydrothieno(2,3-d)-pyrimidin-2-one as crystals having a melting point of 272°–275° C. Recrystallization from acetone gave crystals melting at 247.5°–249° C. The following compounds were prepared similarly:

1-Methyl-4-phenyl-1,2-dihydrothieno(2,3-d)-pyrimidin-2-one, m.p. 256°–257.5° C.

1-Methyl-4-phenyl-6-chloro-1,2-dihydrothieno-(2,3-d)-pyrimidin-2-one, m.p. 136°–140° C.

1-Methyl-4-phenyl-6-nitro-1,2-dihydrothieno-(2,3-d)-pyrimidin-2-one, m.p. 272°–274° C.

1-Cyclopropylmethyl-4-phenyl-1,2-dihydrothieno-(2,3-d)-pyrimidin-2-one, m.p. 191°–191.5° C.

1-Cyclopropylmethyl-4-phenyl-6-nitro-1,2-dihydrothieno(2,3-d)-pyrimidin-2-one, m.p. 216°–218° C.

1-Cyclopropylmethyl-4-phenyl-6-chloro-1,2-dihydrothieno(2,3-d)-pyrimidin-2-one, m.p. 149°–151° C.

1-Methyl-4-(o-fluorophenyl)-1,2-dihydrothieno(2,3-d)-pyrimidin-2-one, m.p. 222°–223° C.

1-Methyl-4-(o-fluorophenyl)-6-chloro-1,2-dihydrothieno(2,3-d)-pyrimidin-2-one, m.p. 192.5°–194° C.

4-(o-Fluorophenyl)-6-methyl-1,2-dihydrothieno-(2,3-d)-pyrimidin-2-one, m.p. 282°–284° C.

1-Methyl-4-(o-chlorophenyl)-1,2-dihydrothieno-(2,3-d)-pyrimidin-2-one, m.p. 225°–226° C.

1-Methyl-4-phenyl-5-methyl-1,2-dihydrothieno(2,3-d)-pyrimidin-2-one, m.p. 281°–283° C.

1-Methyl-4-(o-fluorophenyl)-5-methyl-1,2-dihydrothieno(2,3-d)-pyrimidin-2-one, m.p. 275°–277° C.

1-Methyl-4-(o-fluorophenyl)-6-methyl-1,2-dihydrothieno(2,3-d)-pyrimidin-2-one, m.p. 119°–121° C.

1-Methyl-4-(o-fluorophenyl)-5-methyl-6-chloro-1,2-dihydrothieno(2,3-d)-pyrimidin-2-one, m.p. 175°–176° C.

1-Methyl-4-(o-chlorophenyl)-6-chloro-1,2-dihydrothieno(2,3-d)-pyrimidin-2-one, m.p. 164°–166° C.

1-Methyl-4-phenyl-5-methyl-6-chloro-1,2-dihydrothieno(2,3-d)-pyrimidin-2-one, m.p. 192°–194° C.

1-Methyl-4-(o-chlorophenyl)-5-methyl-1,2-dihydrothieno(2,3-d)-pyrimidin-2-one, m.p. 267.5°–268.5° C.

1-Methyl-4-(o-chlorophenyl)-5-methyl-6-chloro-1,2-dihydrothieno(2,3-d)-pyrimidin-2-one, m.p. 199.5°–200.5° C.

What is claimed is:

1. A thienopyrimidine derivative represented by the formula,

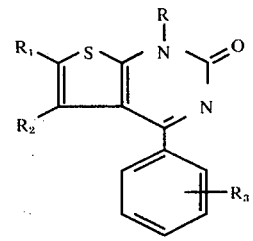

wherein $R_1$ is chlorine, methyl or nitro; $R_2$ is hydrogen or methyl; $R_3$ is hydrogen, chlorine or fluorine; and R is $C_1$-$C_4$ alkyl or cyclopropylmethyl.

2. A compound according to claim 1, which is 1-methyl-4-phenyl-6-chloro-1,2-dihydrothieno[2,3-d]-pyrimidin-2-one.

3. A compound according to claim 1, which is 1-methyl-4-phenyl-6-nitro-1,2-dihydrothieno-[2,3-d]-pyrimidin-2-one.

4. A compound according to claim 1, which is 1-cyclopropylmethyl-4-phenyl-6-nitro-1,2-dihydrothieno[2,3-d]-pyrimidin-2-one.

5. A compound according to claim 1, which is 1-cyclopropylmethyl-4-phenyl-6-chloro-1,2-dihydrothieno[2,3-d]-pyrimidin-2-one.

6. A compound according to claim 1, which is 1-methyl-4-(o-fluorophenyl)-6-chloro-1,2-dihydrothieno[2,3-d]-pyrimidin-2-one.

7. A compound according to claim 1, which is 1-methyl-4-(o-fluorophenyl)-6-methyl-1,2-dihydrothieno[2,3-d]-pyrimidin-2-one.

8. A compound according to claim 1, which is 1-methyl-4-(o-fluorophenyl)-5-methyl-6-chloro-1,2-dihydrothieno[2,3-d]-pyrimidin-2-one.

9. A compound according to claim 1, which is 1-methyl-4-(o-chlorophenyl)-6-chloro-1,2-dihydrothieno[2,3-d]-pyrimidin-2-one.

10. A compound according to claim 1, which is 1-methyl-4-phenyl-5-methyl-6-chloro-1,2-dihydrothieno[2,3-d]-pyrimidin-2-one.

11. A compound according to claim 1, which is 1-methyl-4-(o-chlorophenyl)-5-methyl-6-chloro-1,2-dihydrothieno[2,3-d]-pyrimidin-2-one.

12. A pharmaceutical composition consisting of an uricosurically effective amount of a thienopyrimidine as claimed in claim 1, and a pharmaceutically acceptable carrier.

13. A method of promoting the excretion of uric acid in the urine comprising administering a uricosurically effective amount of a thienopyrimidine as claimed in claim 1.

* * * * *